United States Patent [19]

Sucholeiki

[11] Patent Number: 5,684,130

[45] Date of Patent: Nov. 4, 1997

[54] PROCESS FOR SYNTHESIS OF ORGANIC COMPOUNDS USING MAGNETIC PARTICLES

[75] Inventor: Irving Sucholeiki, Watertown, Mass.

[73] Assignee: Solid Phase Sciences Corporation, Watertown, Mass.

[21] Appl. No.: 462,201

[22] Filed: Jun. 5, 1995

[51] Int. Cl.$^6$ ............................... C07K 2/00; A61K 38/00
[52] U.S. Cl. ..................... 530/333; 530/334; 530/344; 525/54.11
[58] Field of Search ..................... 530/333, 334, 530/344; 525/54.11

[56] References Cited

U.S. PATENT DOCUMENTS

| | | | |
|---|---|---|---|
| 4,339,337 | 7/1982 | Tricot et al. | 252/62.54 |
| 4,638,032 | 1/1987 | Benner | 525/54.11 |
| 4,675,113 | 6/1987 | Graves et al. | 210/635 |
| 4,774,265 | 9/1988 | Ugelstad et al. | 521/55 |
| 5,034,145 | 7/1991 | Leising et al. | 252/62.54 |
| 5,091,206 | 2/1992 | Wang et al. | 427/2 |
| 5,200,270 | 4/1993 | Ishida et al. | 428/403 |
| 5,232,782 | 8/1993 | Charmot et al. | 428/405 |
| 5,268,423 | 12/1993 | Joran | 525/54.11 |
| 5,356,713 | 10/1994 | Charmot et al. | 428/407 |
| 5,502,246 | 3/1996 | Sucholeiki | 562/426 |

OTHER PUBLICATIONS

Pavia et al. "The Generation of Molecular Diversity".
Moos et al., CH33 *Annual Rep. Med. Chem.* (Venutied) vol. 28 pp. 315–324 (1993).
Szymonifka et al, Tetrahedron Letters, vol. 36 No. 10 pp. 1597–1600.

*Primary Examiner*—Cecilia J. Tsang
*Assistant Examiner*—Bennett Celsa
*Attorney, Agent, or Firm*—Sharon L. Day

[57] ABSTRACT

This invention provides a process for the synthesis of a defined chemical entity, i.e., any desired chemical compound, in high yield using a solid support comprising a magnetic particle, in organic solvents. In general, a sequence of chemical synthetic steps are required to prepare the defined chemical entity bound to the particle. The particle comprises a resin bearing a high concentration of substituent pendant functional groups, to which the first reagent employed in the synthetic sequence binds; in subsequent reaction steps further reagents react with the growing chemical intermediate bound to the pendant functional groups until the defined chemical entity is obtained. The particle also comprises smaller paramagnetic or superpara-magnetic particles incorporated within the resin. The magnetic particle therefore responds to imposed magnetic field gradients, permitting ease of manipulation in steps involving removal of organic solvent.

9 Claims, No Drawings

PROCESS FOR SYNTHESIS OF ORGANIC COMPOUNDS USING MAGNETIC PARTICLES

This patent relates a process for the synthesis of a specific defined chemical entity in organic solvents in high yields with the aid of a solid resin support particle. More specifically, the instant invention applies a resin particle derivatized in such a way as to contain bound thereto a high concentration of pendant functional groups for the purpose of anchoring the synthesis of the defined chemical entity. The high concentration of functional groups ensures a high yield for the synthetic process.

BACKGROUND OF THE INVENTION

Chemical synthesis on solid resin particles comprises a process of assembling a desired chemical product covalently bound to a pendant functional group on the resin particle. In general the synthetic process involves a sequence of chemical reactions. Upon completion of the sequence of synthetic steps, yielding the desired product bound to the resin particle, a specific cleavage reagent is applied to release the product into solution. The primary advantage of using such heterogeneous systems for the synthetic process is that the resin particles are easily separable from the solvent in which they are suspended. In this way the growing chemical entity, which is coupled to the resin particles, is readily separated from the solvent and all reagents that had been added thereto to effect the preparation of a given intermediate or the final product, a defined chemical entity. In some applications, the defined chemical entity is left covalently bound to the resin particle, for applications that take advantage of the attributes of the solid particle. Such applications include many assays, as well as developing luminescence or chemiluminescence on the particle when the defined chemical entity is an appropriate fluorescent substance. In many other applications the defined chemical entity is cleaved from the resin particle. After this final cleavage step, the final product, now in solution, is isolated.

This is in contrast to conducting the comparable synthesis in homogeneous solution. In homogeneous syntheses the desired intermediates, and the final product, are dissolved in the same solvent as the reagents that had been added in order to prepare the given substance from the previous intermediate in the synthetic path. As a consequence, after each synthetic step is carried out, the intermediate or final product must by isolated and purified from the solvent and from the other reagents added. This procedure is carried out with varying degrees of efficiency, so that yields of material from starting substance through the intermediates to the final product may well be meager.

In spite of the apparent advantage of conducting synthetic processes coupled to solid particles, namely, ease of separation of the reagents from the growing chemical entity, certain disadvantages are also attendant on this method. Typically the resin is prepared as a highly crosslinked polymer network, with functional groups introduced throughout the three-dimensional domain of the resin particle. A disadvantageous property of such particles is that, in general, they provide low degrees of incorporation of pendant functional groups, termed low loadings. Commonly the loadings of highly crosslinked resin particles are about 0.2 milliequivalents/gm (meq/gm), or less. Furthermore a significant fraction of pendant functional groups in highly crosslinked polymer resins behaves as if the groups are partially occluded from reaction. As a consequence a population of different molecular species develops during a synthetic sequence, ranging all the way from the defined chemical entity through impurities that may lack one or more of the moieties that were intended to be added upon reaction with one reagent or another. It is conceivable that some members of this population may never have progressed past the first stage of reaction, i.e., contain only the starting material bound to the pendant groups. This entire population is then cleaved from the particles, and the mixture must be purified to yield a homogeneous sample containing only the completed final defined chemical entity. If the number of synthetic steps is high, it is likely for these reasons that the yield of the completed final defined chemical entity may be quite low, requiring purification and characterization procedures. And yet a high degree of crosslinking is required in order to maintain the physical integrity of the particles in many organic solvents.

There are many examples of synthetic procedures in which solid particles are in use. Among the earliest was the synthesis of peptides, polypeptides and proteins, for example the chemical synthesis of the enzyme ribonuclease, B. Gutte, et al., *J. Biol. Chem.* 246, 1922, 1971. Since that time solid particles have been extensively used for these purposes, Erickson, B. W., and Merrifield, R. B., in *The Proteins*, 3rd ed., Vol. 2, pp. 105–253, Academic Press, 1977. Another class of solid-supported synthesis is the preparation of oligonucleotides for use in molecular biology and recombinant DNA techniques. (Matteucci and Caruthers, *J. Am. Chem. Soc.*, 103,3185–3191,1981; Gait, M., *Oligonucleotide Synthesis, A Practical Approach*, IRL Press, 1984) In this instance, the particle is frequently a solid, nonporous silica particle whose surface has been modified to accommodate pendant functional groups, the latter then serving as the anchor for the synthesis of the growing oligonucleotide chain. A severe disadvantage of using nonporous particles such as silica is that the effective concentration of pendant groups per unit weight of particles is relatively low, and can only be increased by decreasing the size of the particle, thus increasing the surface-to-volume ratio. Solid particles have also been used in the synthesis of organic compounds, including pharmacologically active substances which are candidates for therapeutic drugs. A final example of a synthetic procedure is development of luminescence or chemiluminescence in a suitable fluorescent molecule bound to the pendant functional groups. In chemiluminescence, the energy of excitation to promote a fluorophore to an excited electronic state is provided by chemical reaction. Chemiluminescence is then the light emitted after such excitation as the excited state decays back to the ground state. (See M. M. Rauhut, in *Chemiluminescence and Bioluminescence*, Plenum Press, N.Y., 1973,p. 451; and K. Gundermann and F. McCapra, *Chemiluminescence in Organic Chemistry*, Springer Verlag, N.Y., 1987)

As noted above, an important advantage of the use of heterogeneous synthesis is the ability to separate the growing desired product intermediates and the final defined chemical entity, bound to the solid particles, from the solvent used for the synthetic reaction and the reagents used to synthesize them, or for solvent rinses. This is commonly done by filtration, using apparatus including a filter to retain the solid particles. As a consequence, synthetic procedures are easily automated, and several assemblies are available from commercial suppliers incorporating automated synthesis of, for example, peptides or oligonucleotides based on separation procedures using filtration. An additional procedure to achieve separation of the solid particles from the solvent in which they are suspended is centrifugation.

In many applications it is desired to prepare a family, or a library, of closely related organic compounds, oligopeptides, oligonucleotides, or the like, using combinatorial methods to effect the incorporation of differing but related moieties. (See, for example, Moos, W. H., Green, G. D., and Pavia, M. R., *Annual Reports in Medicinal Chemistry*, 28, 315, 1993) The products comprising combinatorial libraries thus incorporate moieties, or building blocks, such as amino acid residues or nucleotides, which vary as the moieties introduced at each step are permuted. A disadvantage of automated solid-supported synthetic apparatus incorporating filtration as a separation method is that, although the synthetic procedure can be automated, it can not be easily replicated to include simultaneous operation of a plurality of synthetic chambers each preparing a different member of a library.

An alternative separation procedure is one based on application of magnetic field gradients. A solid support particle which incorporates a paramagnetic or superparamagnetic solid, termed a magnetic particle, will be drawn toward a region of increasing magnetic field gradient, thereby permitting the separation of the particle from the residual solvent and any unexpended reagents, byproducts, or completed final desired product that may be contained therein. Processes for preparing magnetic particles have been described by M. Tricot and J. C. Daniel, FR 79 21342, by J. Ugelstad, T. Ellingsen, A. Berge and O. B. Helgee, U.S. Pat. No. 4,774,265, by F. Leising and G. Torres, U.S. Pat. No. 5,108,636, by D. Charmot, U.S. Pat. No. 5,232,782, and by D. Charmot and C. Vidil, U.S. Pat. No. 5,356,713, and have been applied in oligonucleotide synthesis or other organic synthesis by S. A. Brenner, U.S. Pat. No. 4,638,032.

With magnetic particles it is possible to establish a replicated system for the simultaneous operation of a plurality of synthetic chambers in an apparatus based on the application of magnetic field gradients for separating the particles from the liquid phase. The ultimate extension of replicated synthesis is application to individual beads, or only a small number of individual beads, in a suitable container. Thus magnetic particles offer the possibility of conducting replicate synthesis in a plurality of chambers, leading to the preparation of members of a library of related compounds based on a combinatorial approach.

Conducting synthetic reactions in a plurality of replicated chambers carries with it the requirement of reducing the reaction volume available for each chamber. This therefore limits the amount of solid particles that can conveniently be charged into each chamber. This factor places a premium on maximizing the concentration of pendant groups per unit mass of particles in order to synthesize the maximal amount of completed final desired product in each chamber. Some magnetic particles are nonporous, being prepared by coating a core of magnetic mineral with substances containing pendant functional groups. An example of such particles are those prepared with a coating of silica. As noted above, this procedure risks reducing the available concentration of pendant groups, since they are limited primarily to the surface of the particle. The concentration of pendant groups may only be increased by decreasing the particle size, but below certain size limits the particles become colloidally dispersed and may be difficult to manipulate in a magnetic field gradient. Alternatively, particles of polymeric resins incorporating magnetic cores may have porous structures. A low extent of crosslinking leads to a significant extent of swelling of the polymer network in many organic solvents, resulting in loss of the magnetic particles contained therein. A common solution has been to use a high degree of crosslinking to preserve the integrity of the magnetic particles; this has a disadvantage of conferring minimal porosity to the particle. Therefore, the pendant functional groups available for participating in the synthetic procedure are effectively constrained to the surface of the particle in this case as well. As a result the ability to conduct the synthesis with a high yield is limited in this case.

SUMMARY OF THE INVENTION

The present invention provides a process for the synthesis of a defined chemical entity in organic solvents in high yield. It further provides a process for the synthesis of a defined chemical entity based on the use of solid particles having a high concentration of pendant functional groups per unit mass. Additionally the invention provides a process for the synthesis of a defined chemical entity based on the use of a magnetic field gradient for separating a particle, to which may be bound a growing chemical intermediate or the completed defined chemical entity, from an organic solvent in which it is suspended. Furthermore the invention provides a process for binding suitable fluorescent moieties to magnetic particles, such that the particles become luminescent or chemiluminescent.

DETAILED DESCRIPTION OF THE INVENTION

This invention provides a process for the synthesis of a defined chemical entity in high yield in organic solvents based on the use of composite particles as the solid supports on which the synthesis occurs.

A defined chemical entity is any desired or intended organic chemical substance having a predetermined, preconceived structure as the completed final desired product. Such defined chemical entities may have any of a number of useful applications. They may serve as intermediates in further chemical synthesis. They may be candidates for the discovery or the development of new products having pharmacological activity, thereby having the potential to serve as human therapeutic drugs. They may have applications in biological or biomedical research, assisting in the process of subsequent drug discovery. An additional defined chemical entity is a suitable luminescent substance, in particular, one capable of undergoing chemiluminescence when appropriate chemical reactions are induced to occur in its presence.

The synthetic processes to which this invention applies occur in organic solvents. In general, any organic solvent is envisioned for application in the process of this invention. Examples of common liquids that may serve as solvents in this invention include, but are not limited to, alkanes, cycloalkanes, aromatic hydrocarbons, aralkanes, alcohols including methanol, ethanol and the like, ketones including acetone and 2-butanone, ethers including diethyl ether, tetrahydrofuran and dioxane, halogenated solvents including chloroform and dichloromethane, acids including carboxylic acids such as acetic acid, nitrogenous solvents such as pyridine, piperidine, morpholine, ethanolamine and triethanolamine, methylsulfoxide, formamide, dimethylformamide, and other organic liquids or mixtures thereof.

A solid support is any formed solid particle which is chemically derivatized so that it may serve to bind either a growing chemical entity, or, when the sequence of synthetic steps is completed, the defined chemical entity. A growing chemical entity is any intermediate along the synthetic pathway leading to the final defined chemical entity. The chemical derivatization results in pendant functional groups being bound to the solid particle. The solid support forms the basis for a heterogeneous system, for the solid support comprises one phase, and the solvent with any reagents, synthetic byproducts or the defined chemical entity after it has been cleaved from the solid support (see below), dissolved or suspended therein, comprises a second phase.

In the process of this invention the solid support used comprises a composite particle. The composite particle in turn comprises an outer shell or matrix, fabricated from an outer matrix material, enclosing a plurality of inner particles therein. Each of the inner particles may consist of a single inner matrix material, or each may be comprised of a shell, composed of an inner matrix material, enclosing a core within. In a preferred embodiment of the process of this invention, the outer matrix material and the inner matrix material are each a polymer resin; in particular, the outer matrix material may be a polymer resin with a low extent of crosslinking, and the inner matrix material may the same polymer resin with a higher extent of crosslinking. In a similar preferred embodiment of the process of this invention, the inner particles comprise an inner matrix material as a shell enclosing a magnetic material. The magnetic material may be paramagnetic or superparamagnetic. Substances that may be incorporated as magnetic materials include, for purposes of example only, magnetite, hematite, ferrites of manganese, cobalt and nickel, and alloys comprising cobalt, molybdenum, nickel, samarium and other rare earth metals. In the most preferred embodiment of the process of this invention the composite particle comprises an outer matrix material prepared as a crosslinked polystyrene with a low degree of crosslinking, enclosing a plurality of inner particles, each inner particle comprising an inner matrix material as a shell, prepared as a crosslinked polystyrene with a high degree of crosslinking, and an inner core of magnetite, $Fe_3O_4$. Such composite particles are obtainable from Polymer Laboratories Ltd., Church Stretten, Shropshire SY6 6AX, United Kingdom.

Pendant functional groups are introduced into the composite particle by chemical reaction with suitable reagents which are brought into contact with a suspension of the composite particles. In accordance with an objective of this invention, conditions are chosen to ensure that a high extent of reaction with the materials of the composite particles occurs, yielding composite particles with a high concentration of pendant functional groups per unit mass. Pendant functional groups are introduced into the outer matrix material by the chemical reaction, and may also be introduced into the inner matrix material or the inner shell material, as the case may be. The resulting pendant functional groups represent anchors, or starting points, for the stepwise synthesis of the desired chemical entity on the composite particles.

The chemical nature of the pendant functional groups to be introduced depends on the requirements and exigencies of the synthetic reaction scheme intended to be followed. Desired characteristics of the pendant functional groups include a) ease of derivatization with the first moiety of the desired chemical entity to be introduced in the synthetic reaction scheme, b) ease of cleavage of the chemical bond between the pendant functional group and the first moiety of the desired chemical entity, the cleavage process to be carried out upon completion of the synthetic reaction scheme leading to the completed desired chemical entity being bound to the pendant functional group, and c) ability to carry out the cleavage reaction without affecting the integrity of either the completed desired chemical entity or the materials comprising the composite particles. Without intending to limit the chemical nature of the pendant functional groups, they may be a) carboxyl groups or carboxyalkyl groups, b) primary amino groups, aminoalkyl groups (i.e. primary amines), monoalkylamino or monoalkylaminoalkyl groups (i.e. secondary amines), c) halo groups, especially haloalkyl groups or haloalkaryl groups, d) hydroxyl groups as alkyl alcohols, alkaryl alcohols or phenolic alcohols, or e) aldehyde groups, and the like. In the most preferred embodiment of the process of this invention, the pendant functional group is chosen from the group consisting of chloromethyl, primary aminomethyl, and carboxyl groups.

A high yield of the desired chemical entity is attained in the process of this invention by virtue of a) the incorporation of a high concentration of pendant functional groups per unit mass of composite particles, b) optimization of reaction conditions throughout the synthetic reaction scheme to ensure high step yields, and c) the use of substances with a high degree of porosity or permeability to reagents as the outer matrix material. Without wishing to be constrained by theory, the latter feature should facilitate entry of reagents within the entire domain of the outer matrix material, with minimal inhibition due to the necessity to diffuse through tortuous channels to reach the reactive sites, and minimal steric hindrance from adjacent segments of the outer matrix material. As noted above, in the most preferred embodiment of the process of this invention the composite particle comprises an outer matrix material prepared as a crosslinked polystyrene with a low degree of crosslinking, enclosing a plurality of inner particles each of which comprises an inner matrix material prepared as a crosslinked polystyrene with a high degree of crosslinking, and an innermost core of magnetite. In most cases, the concentration of pendant functional groups on the composite particles applied in the process of this invention is at least 0.4 meq/gm.

In the process of this invention the synthesis of the defined chemical entity occurs according to a sequence of chemical reactions. First, if the solid support is not supplied already bearing pendant functional groups, it is derivatized to incorporate them. Second, the first reagent in the reaction sequence is coupled to the pendant functional groups on the particle. Next, a sequence of steps intended to build up the desired chemical entity in its final form, passing through a series of growing chemical entities bound to the pendant functional groups, is carried out. At the conclusion of this sequence of steps the defined chemical entity is found coupled to the pendant functional groups. In some applications, the defined chemical entity bound to the particles is the intended product, in which case no further steps are carried out. In other applications the defined chemical entity is desired in isolated form, free of the particle on which it was synthesized. In order to harvest the defined chemical entity, the particle to which it is bound is subjected to a final step which cleaves the defined chemical entity from the pendant functional group without itself undergoing any further chemical transformation. The defined chemical entity is now dissolved in the organic solvent used in the cleavage step, and is isolated by appropriate procedures.

After each step in the sequence of chemical reactions required to synthesize the defined chemical entity, the solid particles with the growing intermediate attached to the pendant functional groups thereof is separated from the solvent and from any excess reagents, byproducts, and/or other solutes suspended therein by solid-liquid separation. Washing or rinsing steps may be interspersed between the steps of the sequence of chemical reactions in order to effect complete removal of excess reagents, byproducts, and/or other solutes. The separation can be carried out by a filtration step, in which the solvent and any solutes suspended therein is drawn through the filter, retaining the solid particles on the filter. Separation can also be achieved by centrifugation of the particles. In a preferred embodiment of the process of this invention the separation steps may be carried out on composite particles in which the core of the inner particles comprises a magnetic material, and the composite particles are sequestered to an inner surface of the vessel containing the suspension by a source of a magnetic field gradient imposed on the vessel. The solvent and any solutes suspended therein is removed by aspiration, decantation, or any other suitable technique, leaving the composite particles behind. Removing the magnetic field gradient then permits the ensuing step to be carried out.

Defined chemical entities that may be synthesized by the process of this invention include a broad range of compounds that are, or have the potential of being, pharmacologically active substances. They may also be substances with utility in conducting experiments in biological and biomedical systems, or they may be substances with utility as intermediates in the further synthesis of an ultimate defined chemical entity, or as reagents in any in vitro diagnostic test. Without intending to limit the identity of such compounds in any way, examples include substances which may inhibit the activity of specific enzymes, or serve as substrates for a specific enzyme, or interfere with binding between a ligand and a receptor, or serve as an antagonist for a receptor by occupying a binding site without inducing a physiological response. Such compounds may include oligopeptides, polypeptides, analogs of oligopeptides and polypeptides, proteins, oligoribonucleotides, oligodeoxyribonucleotides, phosphorothioate analogs of oligoribonucleotides and oligodeoxyribonucleotides, oligosaccharides and polysaccharides. They may also be suitable luminescent molecules, including those capable of undergoing chemiluminescence.

A still further general application of the process of this invention is preparation of a library of related defined chemical entities using a combinatorial approach to the sequence of chemical reactions to be carried out. A library is a set of related defined chemical entities in which the structures of the defined chemical entities are varied in systematic ways. At various steps i, j, and so on, of a sequence of synthetic reactions, one of a plurality of related reagents, $n_i$, $n_j$, and so on is introduced into an replicated assembly of reaction vessels. The integers $n_i$, $n_j$, and so on represent the total number of related reagents used in each step. In such a synthesis, the total number of distinct defined chemical entities in the library would be the product of the integers: $n_i \times n_j \times \ldots$ In a preferred implementation of the present invention a process is provided for separating composite resin particles comprising inner particles with a core of magnetic material, and suspended in an organic solvent in a plurality of vessels, from the organic solvent and any excess reagents, byproducts, and/or other solutes suspended therein using magnetic field gradients. Any replicated assembly of a plurality of vessels containing such magnetic composite particles may be subjected to a magnetic field gradient in unison to effect the separation from the organic solvent in which they are suspended simultaneously. If, at various steps in the sequence of chemical reactions a different but related reagent is used in each vessel of the assembly, rather than a unique reagent, the intermediates synthesized at such steps will have different, but related, structures. As the sequence of chemical reactions progresses, the application of different but related reagents will produce a set of defined chemical entities having permuted arrangements of the moieties introduced by exposure to the various sets of reagents. I.e., a set comprising members of a library of defined chemical entities will have been prepared. In each synthesis of defined chemical entities conducted, the maximum number of different defined chemical entities that may be prepared is the same as the number of vessels in the assembly. Without wishing to limit the way in which combinatorial synthesis might be implemented by the process of this invention, the format of multi-well microtiter plates is one that is well adapted for this purpose.

In order further to specify the process of this invention, the following examples are provided. It will be recognized by those skilled in the art that these examples represent only specific implementations of the process of the invention. They in no way limit its scope.

EXAMPLE 1

Magnetic Separation Procedure. Magnetic composite particles comprising a plurality of inner particles of highly crosslinked polystyrene enclosing a core of magnetite, and an outer matrix of low-crosslinked polystyrene 1 were obtained from Polymer Laboratories Ltd., Church Stretten, Shropshire SY6 6AX, United Kingdom. Such magnetic composite particles were separated from any solvent in which they were suspended by applying a magnetic field gradient using a BioMag Separator (Advanced Magnetics, Cambridge, Mass.). When involving quantities of <0.2 grams of magnetic composite particles, the BioMag Separator was applied to the side of the reaction vessel, resulting in the particles adhering to the inner surface opposite the position of the BioMag Separator. The solvent was then siphoned off. The BioMag Separator was removed and fresh solvent added and the mixture shaken. This process was repeated for the total number of wash steps desired. For quantities of magnetic composite particles >0.2 grams, a BioMag Separator was applied to the bottom of the reaction vessel, typically composed of a stoppered Erlenmeyer flask. The magnetic composite particles adhered to the inner surface of the flask opposite the position of the BioMag Separator. The solvent was then siphoned from the top of the flask down to roughly a few millimeters from the surface of the particles. Washes with additional solvent were then carried out, for as many steps as desired.

EXAMPLE 2

Synthesis Of Carboxylated Composite Magnetic Particles (Scheme 1). To a 100 mL round bottom flask was added 2.8 grams of 1 and the solid was placed under a nitrogen atmosphere. To the

Scheme 1

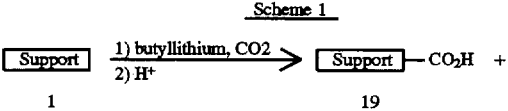

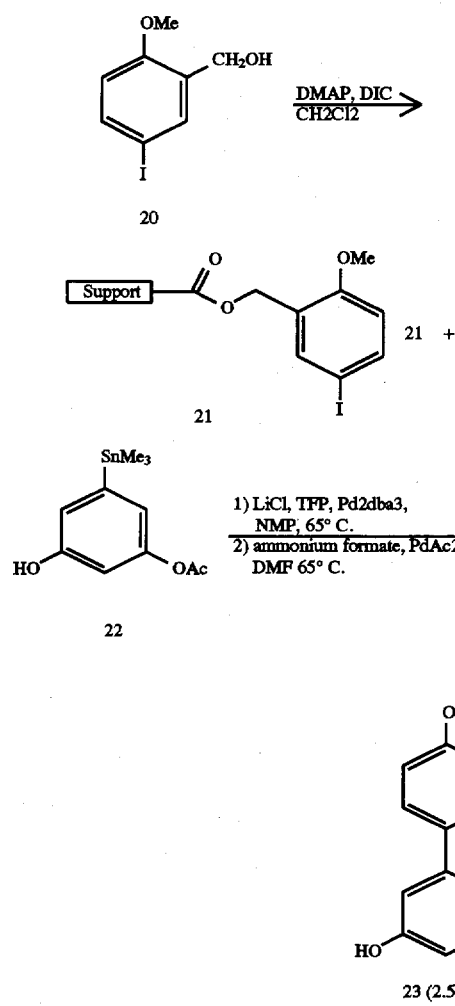

solid was added 12 mL of cyclohexane, 5.8 mL (38.5 mmole) of tetramethylethylenediamine and 20 mL of 1.7M (39.1 mmole) of N-butyllithium, and the mixture stirred at room temperature for 5–10 minutes. The mixture was then heated at 65° C., under a nitrogen atmosphere for 5 hours. The reaction mixture was allowed to cool to room temperature, the top liquid was siphoned off, and 15 mL of cyclohexane was added. The particles were stirred for 1 minute and the top liquid was siphoned off. 15 mL of tetrahydrofuran (THF) was then added and the mixture stirred for 1 minute. The liquid was again siphoned off and 15 mL of THF was again added. The mixture was then cooled in a dry ice-acetone bath and carbon dioxide was bubbled through the reaction mixture for 20 minutes. To the reaction mixture was then added 15–20 grams of dry ice with stirring, and the reaction was allowed to warm to room temperature. Stirring was continued until all the dry ice had sublimed. After allowing the particles to settle, the solvent was siphoned off. The particles were washed with 15 mL of 50% methanol-THF and then the top layer siphoned off. 80 mL of a 2N HCl solution was then added to the particles. The mixture was filtered and the particles washed with methanol and then methylene chloride and then placed under pump vacuum to give 2.9 grams of composite magnetic particles with pendant carboxyl groups 19 as a gray solid.

EXAMPLE 3

Esterification of Carboxylated Composite Magnetic Particles (Scheme 1). To a peptide synthesis vessel containing 1.1 grams of carboxylated magnetic particles 19 prepared as in Example 2 was added a solution of 1.5 grams (5.68 mmole) 2-iodo-5-methoxy-benzyl alcohol 20 in 5 mL of methylene chloride, a solution of 0.24 grams (1.96 mmole) of dimethylaminopyridine (DMAP) in 3 mL of methylene chloride and 0.5 mL (3.19 mmole) of diisopropylcarbodiimide (DIC) and the mixture shaken at room temperature for 15 hours. The resin was filtered and washed with methylene chloride (4×), methanol (6×), methylene chloride (4×), methanol (6×) and methylene chloride (3×) in that order. The solid was then place under pump vacuum to give 1.3 grams of the iodinated benzyl resin-carboxylate ester 21. The level of substitution was determined by iodine elemental analysis to be 0.54 mmoles iodine/gram of bead.

EXAMPLE 4

Biaryl Coupling and Reductive Cleavage of Carboxylated Magnetic Beads (Scheme 1). To 0.35 grams (0.19 mmole) of the benzyl ester magnetic beads 21 was added 25 mg (0.10 mmole) of trifurylphosphine (TFP), 0.18 grams (0.56 mmole) of trimethylphenyl tin 22, 36.8 mg (0.78 mmole) of lithium chloride and 44 mg (0.05 mmole) of tris (dibenzylideneacetone)dipalladium (Pd$_2$dba$_3$). To the mixture was added 3 mL of N-methylpyrrolidinone (NMP), and the mixture was heated at 65° C. under closed atmosphere for 22 hours. The resin was then washed using the magnetic separation procedure specified in Example 1. To the resin was then added 3 mL of dimethylformamide (DMF), 70 mg (0.31 mmole) of palladium acetate and 0.19 mL (1.5 mmole) of 8M ammonium formate. The mixture was heated at 65° C. for 20 h, cooled to room temperature and filtered to give 2.5% of 3,5-dihydroxy-3'-methyl-4'methoxybiphenyl 23. The yield of biphenyl product was determined using reversed-phase HPLC and 254 nm detection. A measured volume of the reaction mixture and a solution of 4-amino-3-nitrophenol (used as an internal standard) were injected into the HPLC and the chromatogram peak areas recorded. Correlation was measured using solution-made biphenyl standards.

EXAMPLE 5

Scheme 2

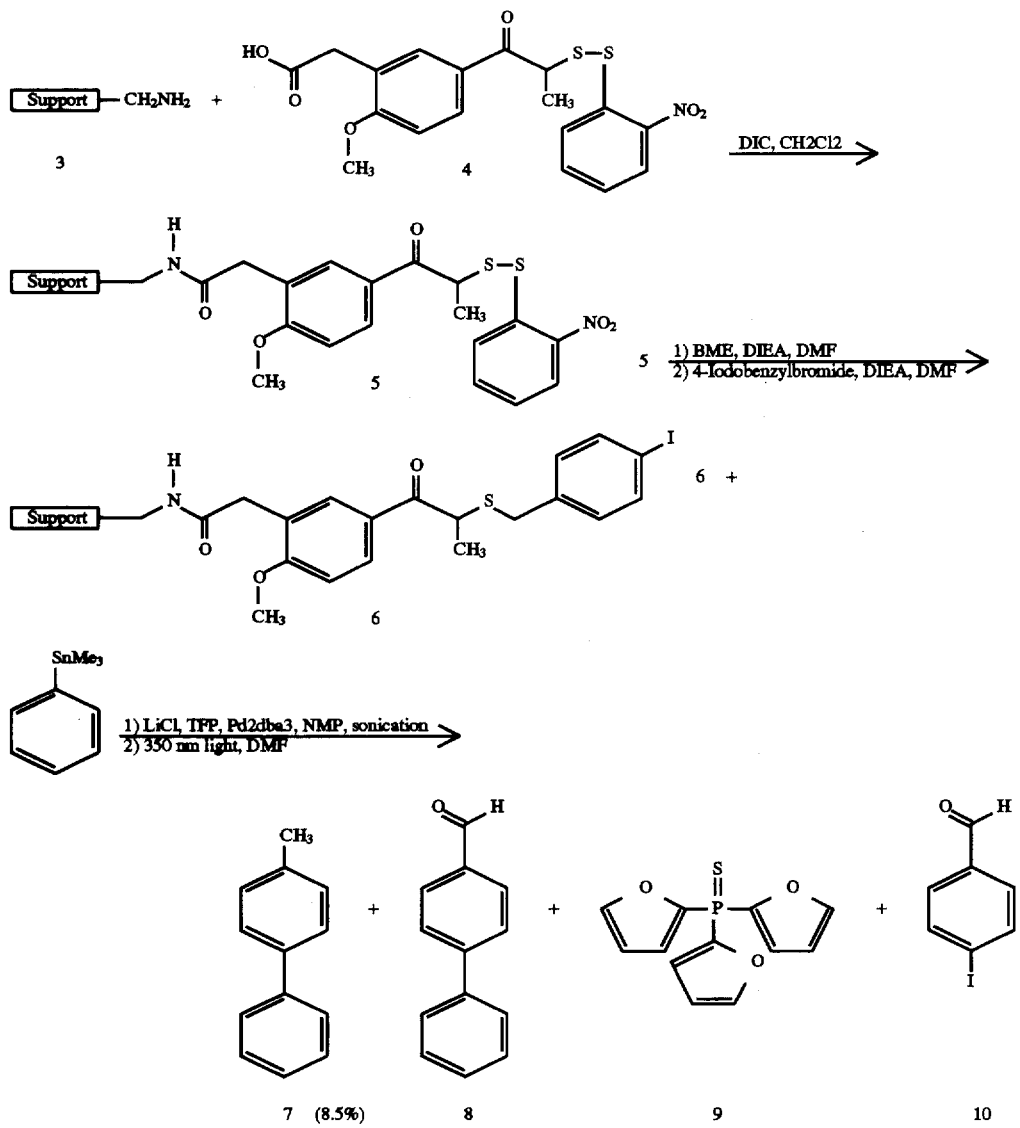

Synthesis of a 4-Iodobenzylthioether Bound to a Linking Moiety on Aminomethyl Magnetic Composite Particles (Scheme 2). a) Coupling of Linker to Aminomethyl Magnetic Composite Particles 5. Magnetic composite particles bearing aminomethyl pendant functional groups were obtained from Polymer Laboratories Ltd., Church Stretten, Shropshire SY6 6AX, United Kingdom. They were found to contain 0.69 mmoles aminomethyl groups/gram particles as determined by the quantitative ninhydrin procedure of Sarin, V. K.; Kent, S. B. H.; Tam, J. P.; Merrifield, R. B. Anal. Biochem. 117, 147, 1981. To 1.0 gram aminomethyl magnetic composite particles 3 was added 100 mL of tetrahydrofuran (THF) and the mixture shaken for 4 hours. The mixture was then filtered and washed three times with methylene chloride. To the filtered resin was then added 60 mL of methylene chloride and 2 mL (11.5 mmole) of diisopropylethyl amine (DIEA) and the mixture shaken for 10 minutes. The mixture was then filtered and washed three times each with methylene chloride. To the filtered particles was then added 60 mL of methylene chloride and a solution of 1.3 grams (3.2 mmole) of (+−)-2-methoxy-5-[2-[(2-nitrophenyl)dithio]-1-oxopropyl)phenyl acetic acid disulfide linker (NpSSMpact, 4) in 3 mL of dimethylformamide (DMF) and the mixture shaken for 30 seconds. To the mixture was then added 0.5 mL (3.2 mmoles) of DIC and the mixture shaken in the dark for 13 hours. The mixture was then filtered and washed with methylene chloride (4×), methanol (3×) and then again with methylene chloride (3×). The filtered resin was then placed under pump vacuum to give 1.4 grams of NpSSMpact-substituted aminomethyl particles 5. Quantitative ninhydrin determination of the free amines remaining after coupling gave a level of substitution of 0.68 mmoles of linker/gram.

b) Deprotection and Alkylation of Particles 5 to give Thioether Particles 6. To 1.4 grams (0.95 mmole) of dry NpSSMpact-substituted particles 5 was added 10 mL of THF and the mixture shaken for 3 hours. The solid was filtered and washed with DMF and then filtered again. To the resin was added 10 mL of DMF, 1 mL of β-mercaptoethanol and 2 mL of DIEA and the mixture shaken for 10 minutes.

The resin was washed with DMF (4×), methanol (2×), DMF (3×), CH₂Cl₂ (2×) and then DMF (2×) in that order. To the resin was then added 10 mL of DMF, 1 mL of β-mercaptoethanol (BME) and 2 mL of DIEA and mixture shaken for 10 minutes. The previous wash protocol was then repeated. To the resin was then added 1.43 grams (4.81 mmole) of 4-iodobenzylbromide dissolved in 10 mL of DMF and 1.5 mL (8.61 mmole) of DIEA and the mixture shaken in the dark for 14 hours. The particles were then filtered and washed with DMF (4×), methanol (3×) and methylene chloride (4×) and then placed under pump vacuum to give 1.34 grams of the iodobenzylthioether 6. The level of substitution by the iodobenzyl group was determined by iodine elemental analysis to be 0.21 mmoles of iodine/gram.

EXAMPLE 6

Solid-phase Biaryl Coupling and Photolytic Cleavage of Particles 6 (Scheme 2). To a test tube was added 147 mg (0.031 mmole) of iodobenzylthioether magnetic particles 6 and 2 mL of NMP and the mixture sonicated using a Heat Systems sonicator, model XL2020 (at a power setting=2) for 2 hours following a program of sonicating on for 30 seconds and off for 30 seconds. To the mixture was then added 13.3 mg (0.28 mmole) of LiCl, 17.4 mg (0.018 mmole) of Pd₂dba₃, 4.9 mg (0.021 mmole) of trifurylphosphine, 0.1 mL The particles were then transferred to a quartz test tube containing a stir bar. To the resin was then added 5 mL of distilled DMF and mixture irradiated, while stirring, at 350 nm for 6 hours. The beads were then separated using a Bio Mag Separator to give a mixture of four major products, with one of these being a 8.5% yield of 4-phenyltoluene 7, determined according to the analysis described in Example 4 (F. W. Forman and I. Sucholeiki, *J. Org. Chem.* 60, 523, 1995).

EXAMPLE 7

Stepwise Synthesis of Glycyl-Alanyl-Isoleucyl-Alanyl-Linker on Magnetic Composite Particles (Scheme 3). a) Coupling and Deprotection of Rink Amide Linker (11) according to Rink, H.; Tetrahedron Lett., 28, 3787, 1987. To 1.0 grams (0.68 mmole) of aminomethyl magnetic composite particles 3 (Example 5) was added 60 mL of methylene chloride and 2 mL (11.4 mmole) of DIEA and the mixture shaken for 1 min. The mixture was filtered and washed three times with methylene chloride. To the filtered particles was then added 60 mL of methylene chloride, 1.7 grams (3.15 mmole) of p-[(R,S)-a-[1-9H-fluoren-9-yl)-methoxbenzyl]-phenoxyacetic acid (Fmoc) linker 11 dissolved in 5 mL of DMF and

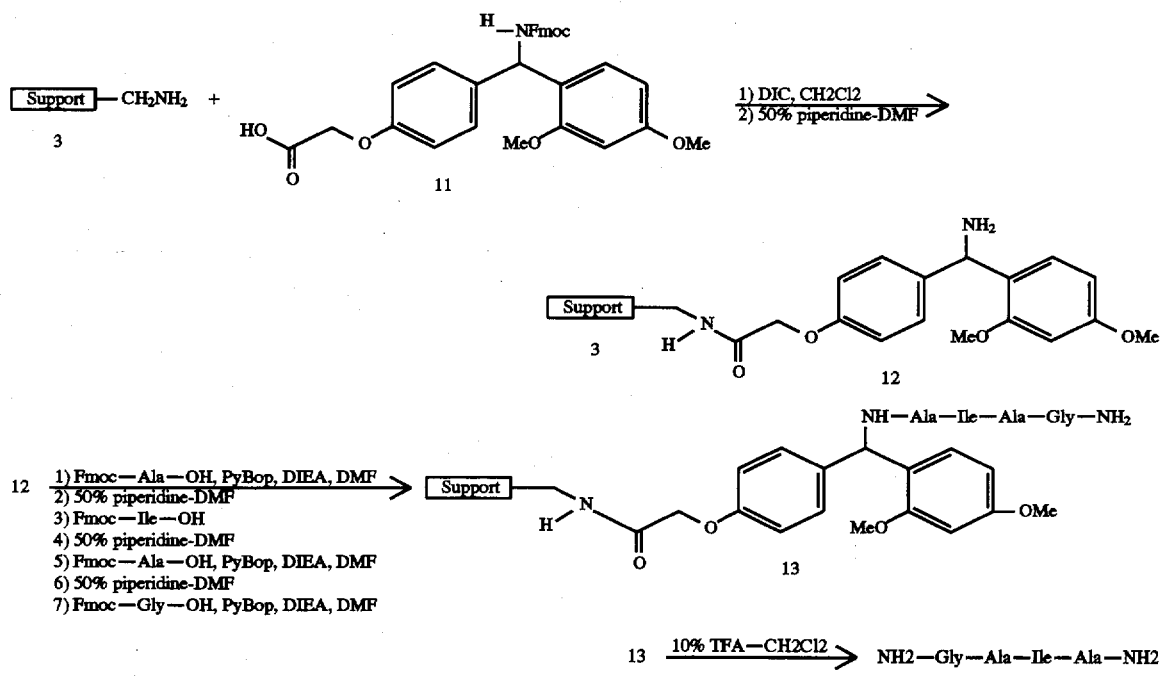

(0.54 mmole) of trimethylphenyltin and an additional 2 mL of NMP. The mixture was then sonicated in the dark, under a closed atmosphere, for a period of 2 hours (at a power setting=5) using the previous sonication program. The resin was then separated using a Bio Mag Separator following the magnetic separation procedure of Example 1. The particles were washed with DMF (5×), methanol (5×) and methylene chloride (5×) in that order. The magnetic particles were then placed under pump vacuum to give 128 mg of resin.

0.5 mL (3.19 mmole) of DIC in that order. The mixture was shaken for 11 hours, and then filtered and washed with methylene chloride (3×). To the particles was added 60 mL of methylene chloride, 1 mL (10.5 mmole) of acetic anhydride and 2 mL (11.4 mmole) of DIEA and the mixture shaken for 2 hours. The particles were then washed with methylene chloride (4×), methanol (3×) and methylene chloride (3×) in that order. The solid was place under pump vacuum to give 1.66 grams of the Fmoc protected, Rink amide-coupled magnetic composite particles. The level of substitution was determined to be 0.68 mmole/gram, by a Fmoc spectrophotometric assay according to Green, J.; Bradley, K. Tetrahedron 49, 4141, 1993.

b) Synthesis of Gly-Ala-Ile-Ala bound to Rink amide linker 13. In this Example, a-N-Fmoc-substituted amino acids are abbreviated Fmoc-Xxx, where Xxx is the conventional three-letter abbreviation for any of the amino acids. To 0.51 grams (0.34 mmole) of Fmoc protected magnetic particles was added 15 mL of 50% piperidine in dimethylformamide and mixture shaken for 40 minutes. The particles were separated and washed with DMF (3x), methanol (3x), $CH_2Cl_2$ (1x) and DMF (1x), following the magnetic separation procedure of Example 1.

To the deprotected particles 12 (0.34 mmole) was added a solution of 0.35 grams (1.1 mmole) of α-N-Fmoc-Ala in 5 mL of DMF, 0.5 grams (1.1 mmole) of benzotriazole-1-yl-oxy-tris-pyrrolidino-phosphonium-hexafluorophosphate (PyBop) in 5 mL of DMF, 0.4 mL (2.3 mmole) of DIEA and an additional 5 mL of DMF and the mixture shaken for 4 hours. The particles were washed with DMF (3x), methanol (3x), $CH_2Cl_2$ (1x) and DMF (2x) following the magnetic separation procedure of Example 1. The particles were then deprotected using 15 mL of 50% piperidine in DMF for 35 minutes. Coupling and deprotection of Fmoc-Ile, Fmoc-Ala and Fmoc-Gly, in that order, was accomplished in the same manner as just described for the first Fmoc-Ala reaction. All the washes were done following the magnetic separation procedure of Example 1. This procedure gave after drying under pump vacuum 0.46 grams of Gly-Ala-Ile-Ala-linker magnetic composite particles 13.

EXAMPLE 8

Cleavage of Gly-Ala-Ile-Ala 14 Off Magnetic Composite Particles (Scheme 3). To 0.46 grams of dried resin 13 was added 20 mL of a 10% trifluoroacetic acid (TFA) in methylene chloride and the mixture shaken for 40 minutes. The particles were magnetically separated and the liquid was siphoned off. To the particles was added another 15 mL of 10% TFA-$CH_2Cl_2$ solution and the mixture shaken for 5 minutes. The particles were again magnetically separated. The liquid was siphoned off and combined with the previous acid wash, and the volatile components removed under reduced pressure to give an oil. The oil was precipitated from diethyl ether to give 33 mg (20%) of 14 as the TFA salt: $^1$H NMR (d-DMSO) δ 0.83–0.85 (m, 6H), 1.08–1.1 (m, 1H), 1.22 (t, 6H, J=7.8 Hz), 1.40–1.44 (m, 1H), 1.70–1.77 (m, 1H), 3.57 (br s, 2H), 4.12–4.21 (m, 2H), 4.40–4.50 (m, 1H), 6.98 (s, 1H), 7.28 (s, 1H), 7.75 (d, 1H, J=7.1 Hz), 7.96–8.05 (m, 4H), 8.50 (d, 1H, J=7.1Hz); amino acid analysis Gly (1.0), Ala(2.2), Ile(1.1); FABMS (M+H) Calcd for $C_{14}H_{27}N_5O_4$ m/e 330.2141, measured 330.2141.

Anal. Calcd for $C_{14}H_{27}N_5O_4 \cdot 1.35$ TFA: C, 41.50; H, 5.91; N, 14.48; F, 15.91. Found: C, 41.17; H, 5.80; N, 12.98; F, 15.87.

EXAMPLE 9

Scheme 4

-continued
Scheme 4

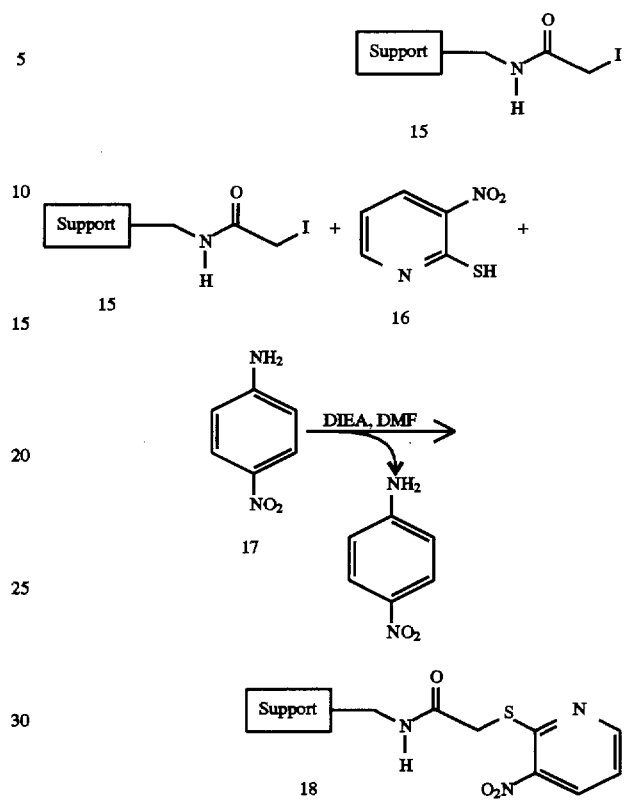

Preparation of Iodoacet-(N-methylamido) Magnetic Composite Particles 15 (Scheme 4). To 0.2 grams (1.0 mmole) of iodoacetic acid was added 10mL of methylene chloride and the mixture sonicated until dissolution was complete. To the solution was added 0.15 mL (1.0 mmole) of DIC and the solution was stirred for 5–10 minutes. The mixture was then filtered through a medium porosity fritted glass funnel and the solid washed with an additional 5 ml of methylene chloride. The liquid filtrate was then added to 0.51 grams (0.34 mmole) of magnetic composite particles bearing aminomethyl pendant functional groups (Polymer Laboratories Ltd., Example 5) 3 and the mixture was shaken for 15 hours. The mixture was then filtered and washed with $CH_2Cl_2$ (3x), methanol (3x) and $CH_2Cl_2$ (5x) and then placed under pump vacuum to give 0.59 grams of magnetic composite particles bearing iodoacet-(N-methylamido) pendant functional groups 15. The level of substitution was determined by iodine elemental analysis to be 0.64 mmoles iodine/gram.

EXAMPLE 10

Affinity Purification using Iodoacet-(N-methylamido) Magnetic Composite Particles 15 (Scheme 4). This Example demonstrates specific reaction of derivatized magnetic composite particles with one reactive substance in a mixture containing two such substances. To 16.8 mg of bis-(3-nitro-2-mercaptopyridine) disulfide (0.054 mmole) (synthesized following Matsueda, R.; Walter, R. Int. J. Peptide Protein Res. 16, 392, 1980 and Matsueda, R. Aiba, K. Chem. Lett., 951, 1978) was added 14 mg (0.092 mmole) of dithiothreitol (DTT), 8 mL of DMF and 0.2 mL (1.14 mmole) of DIEA and the mixture stirred until solution was complete. To the dark orange solution was then added 7.2 mg (0.058 mmole) of 4-nitroaniline. To the solution was then added 0.3 grams (0.19 mmole) of magnetic composite particles bearing iodoacet-(N-methylamide) pendant functional groups 15 (Example 9) and the mixture shaken for 2 hours. Aliquots were periodically taken and separated using reversed-phase HPLC. After 26 minutes, 98% of the mercaptan 16 was found to bind to the particles. The particles was then separated using the magnetic separation procedure of Example 1 and the particles washed repeatedly with DMF, methanol and methylene chloride. Elemental analysis of the dry particles 18 gave a sulfur substitution level of 0.48 mmoles sulfur/gram and an iodine substitution level of 0.12 mmoles iodine/gram.

EXAMPLE 11

Binding of the Fluorophore Rose Bengal to Magnetic Composite Particles. Magnetic composite particles bearing chloromethyl pendant functional groups 2 (Scheme 2), shown by elemental analysis to contain 0.96 mmol Cl/gm, were obtained from Polymer Laboratories Ltd., Church Stretten, Shropshire SY6 6AX, United Kingdom. 1.0 grams of chloromethyl particles 2 and 2.0 grams of rose bengal were added to a vial, together with 20 mL DMF. The mixture was sonicated for 8 hours, then it was filtered and the particles were rinsed repeatedly with DMF, methanol, THF, methylene chloride, and finally with methanol. The particles were dried under vacuum overnight to give 1.0 gram of red rose bengal-coupled magnetic composite particles 24. Iodine elemental analysis gave a loading of 0.092 mmoles iodine/gram particles (equivalent to 0.023 mmole rose bengal/gram particles).

EXAMPLE 12

Chemiluminescence of Rose Bengal-Coupled Magnetic Composite Particles. 10.0 mg of rose bengal-coupled magnetic composite particles 24, 40 mg bis(pentachlorphenyl) oxalate (0.068 mmoles) and 2 mL of dimethylphthalate and 0.1 mL of 30% hydrogen peroxide were added to a vial. The particles were found to emit orange-red light, which continued for more than one hour, when viewed in the dark.

I claim:

1. A process for synthesizing a defined chemical entity in high yield in organic solvent, using a composite polystyrene resin particle as a solid support, said composite polystyrene resin particle comprising an outer polystyrene resin matrix enclosing a plurality of inner particles, each of said inner particles comprising an inner polystyrene resin shell having a higher degree of cross-linking than said outer polystyrene matrix, said polystyrene resin shell enclosing a solid, non-resin core, said solid, non-resin core selected from the group consisting of a paramagnetic material and a superparamagnetic material, and said composite polystyrene resin particle bearing a plurality of pendant functional groups, said pendant functional groups covalently bound to said outer polystyrene resin matrix, said pendant functional groups providing said composite polystyrene resin particle with a loading capacity of greater than 0.2 mmoles of said pendant functional groups/gram of composite polystyrene resin particle, said process comprising sequentially repeating the steps of:

a) providing said composite polystyrene resin particle in sufficient quantity to achieve a plurality thereof;

b) contacting said plurality of composite polystryene resin particles with a suspension or solution comprising at least one reactive substance in said organic solvent, under conditions appropriate for chemical reaction to proceed, and c) separating said plurality of composite polystyrene resin particles from said suspension or solution, as many times as required in order to synthesize said defined chemical entity bound covalently to said pendant functional groups.

2. A process for synthesizing and isolating a defined chemical entity in high yield in organic solvents, using a composite polystyrene resin particle as a solid support, said composite polystyrene resin particle comprising an outer polystyrene resin matrix enclosing a plurality of inner particles, each of said inner particles comprising an inner polystyrene resin shell having a higher degree of cross-linking than said outer polystyrene matrix, said polystyrene resin shell enclosing a solid, non-resin core, said solid, non-resin core selected from the group consisting of a paramagnetic and a superparamagnetic material, and said composite polystyrene resin particle bearing a plurality of pendant functional groups, said pendant functional groups covalently bound to said outer polystyrene resin matrix, said pendant functional groups providing said composite polystyrene resin bead with a loading capacity of greater than 0.2 mmoles of said pendant functional groups/gram of said composite polystyrene resin particle;

said process comprising sequentially repeating the steps of:

a) providing said composite polystyrene resin particle in sufficient quantity to achieve a plurality thereof;

b) contacting said plurality of composite polystyrene resin particles with a suspension or a solution comprising at least one reactive substance in an organic solvent, under conditions appropriate for chemical reaction to proceed, and c) separating said plurality of composite polystyrene resin particles from said suspension or a solution, as many times as required in order to synthesize said defined chemical entity bound covalently to said pendant functional groups, and further comprising the steps of d.) contacting said composite polystyrene resin particles with a suspension or solution of at least one final reactive substance in a final organic solvent, said final reactive substance or substances being capable of cleaving said defined chemical entity from said plurality of pendant functional groups and releasing said defined chemical entity into said suspension or solution in said final organic solvent, e.) separating said suspension or solution containing said defined chemical entity in said final organic solvent from said composite polystyrene resin particles, and f.) isolating said defined chemical entity.

3. The process of claims 1 or 2 wherein said paramagnetic or superparamagnetic material consists of magnetite.

4. The process of claims 1 or 2 wherein said steps of separating said composite polystyrene resin particles from said suspension or solution in said final organic solvent comprise exposing said suspension or solution to a magnetic field gradient and drawing off said final organic solvent.

5. The process of claims 1 or 2 wherein said plurality of pendant functional groups is chosen from the group consisting of primary amino, secondary amino, alkoxy, halo, alkylhalo, carboxy and alkylcarboxy.

6. The process of claim 1 or 2 wherein said plurality of pendant functional groups is amino or aminomethyl.

7. The process of claim 1 or 2 wherein said plurality of pendant functional groups is chloro or chloromethyl.

8. The process of claim 1 or 2 wherein said plurality of pendant functional groups is carboxy or carboxymethyl.

9. The process of claim 1 wherein said defined chemical entity comprises a luminescent moiety or a chemiluminescent moiety.

* * * * *